United States Patent [19]
Chu et al.

[11] Patent Number: 6,084,109
[45] Date of Patent: Jul. 4, 2000

[54] PROCESS FOR THE PREPARATION OF PYROMELLITIC DIANHYDRIDE

[75] Inventors: Shiao-Jung Chu, Hsin Chu; Chian-Liang Hwang, Kao Hsiung, both of Taiwan

[73] Assignee: Chinese Petroleum Corp., Taipei, Taiwan

[21] Appl. No.: 09/293,275

[22] Filed: Apr. 16, 1999

[30] Foreign Application Priority Data

Jul. 31, 1998 [TW] Taiwan ................................. 87112653

[51] Int. Cl.⁷ ................................................. C07D 493/00
[52] U.S. Cl. ............................................................ 549/239
[58] Field of Search ..................... 549/239, 236

[56] References Cited

U.S. PATENT DOCUMENTS

| | | | |
|---|---|---|---|
| 4,665,200 | 5/1987 | Nakanishi et al. | 549/239 |
| 4,694,089 | 9/1987 | Kosaka et al. | 549/239 |
| 5,387,699 | 2/1995 | Wagner | 549/239 |

FOREIGN PATENT DOCUMENTS

| | | |
|---|---|---|
| 0 649 677 A1 | 4/1995 | European Pat. Off. . |
| 0 676 400 A2 | 10/1995 | European Pat. Off. . |
| 0 676 400 A3 | 10/1995 | European Pat. Off. . |

*Primary Examiner*—Amelia Owens
*Attorney, Agent, or Firm*—Beyer Weaver Thomas & Nguyen LLP

[57] ABSTRACT

The present invention relates to a process for preparing pyromellitic dianhydride via an oxidation in gas phase under normal pressure. The process is characterized in that a catalyst system is used, which catalyst system comprises a catalyst which is a mixture of vanadium and tungsten oxides; a catalyst support comprising rutile and at least one material selected from the group consisting of tungsten carbide, silicon carbide and a mixture thereof; and a cocatalyst comprising oxides of manganese, antimony, bismuth, phosphorus, copper, aluminum, titanium or a mixture thereof, an oxide of an element of the VIIIB group of the periodic table, and an oxide of an alkali metal and/or alkaline earth metal. In this process, pyromellitic dianhydride is produced from a feedstream containing 1,2,4,5-tetraalkylbenzene in a gas flow rate of 4,000~12,000 hr⁻¹ via a selective oxidation at 300~450° C. in the presence of air which acts as an oxidant.

10 Claims, No Drawings

PROCESS FOR THE PREPARATION OF PYROMELLITIC DIANHYDRIDE

The present invention relates to a process for the preparation of pyromellitic dianhydride from 1,2,4,5-tetraalkylbenzene via selective oxidation and the subsequent dehydration in gas phase under normal pressure. In this process a catalyst system which comprises a support, a catalyst and a cocatalyst is employed, wherein a mixture of vanadium and tungsten oxides is main active catalyst source; a mixture of rutile and at least one material selected from the group consisting of tungsten carbide, silicon carbide and a mixture thereof is support; and a combination of an oxide of an element of the I A and/or II A group of the periodic table, an oxide of manganese, antimony, bismuth, phosphorus, copper, aluminum, titanium or a mixture thereof, and an oxide of an element of the VIII B group of the periodic table is cocatalyst. In this catalyst system, the catalyst and cocatalyst in combination has the following formula:

$$VM_{Ia}M_{IIb}M_{IIIc}M_{IVd}O_x$$

wherein:

V is vanadium;

$M_I$ is tungsten;

$M_{II}$ is manganese, antimony, bismuth, phosphorus, copper, aluminum, titanium or a mixture thereof;

$M_{III}$ is an element of the VIIIB group of the periodic table;

$M_{IV}$ is an alkali metal and/or an alkaline earth metal; and

X is a value within the range of from 7 to 40 "a" is a value within the range of from 0.1 to 10; "b" is a value within the range of from 0.01 to 1; "c" is a value within the range of from 0 to 0.5; and "d" is a value within the range from 0.01 to 0.6.

In the presence of the abovesaid catalyst system, by using molecular oxygen in air as the oxidant, pyromellitic dianhydride is produced from a gaseous feedstream with a space-velocity of 4,000~12,000 hr$^{-1}$ containing 1,2,4,5-tetraalkylbenzene via selective oxidation and the subsequent dehydration at a temperature of 300~450° C.

Pyromellitic dianhydride is applied as a curing agent for epoxy resins to be formed into materials having good heat resistance and useful for producing huge moldings, or materials having good insulating property useful for producing electric devices. Pyromellitic dianhydride is also useful as a cross-linking agent for polyurethane resins and as an additive for coatings. In addition, pyromellitic dianhydride may be copolymerized with aromatic diamines into an engineering plastic of the polyimide series which is a new synthetic material having good resistance to high or low temperature, radiation and impact, and good electrical and mechanical properties. Said engineering plastic is very suitable for the production of electric or mechanical device parts, insulating films of cables, semiconductor and microelectronic device parts, and substrates for the soft boards of printed circuit boards. This engineering plastic thus plays an important role in the fields of electric and aerial engineerings.

Pyromellitic dianhydride can be prepared by oxidizing 1,2,4,5-tetramethylbenzene in liquid phase at 100~250° C., under 100~450 psig with cobalt, manganese and bromine as catalysts (or with nitric acid as the catalyst), then dehydrating the thus obtained pyromellitic acid into pyromellitic dianhydride. As an alternative, 1,2,4,5-tetramethylbenzene can be directly subjected to selective oxidation and the subsequent dehydration in gas phase to form pyromellitic dianhydride. In the liquid-phase oxidation, complicated procedures are involved, and the crude pyromellitic dianhydride need be refined into a product with high purity. Also, the liquid-phase oxidation is accompanied by the problems of corrosion in apparatus and disposal of waste water. Therefore, gas-phase oxidation is usually adopted in the mass production of pyromellitic dianhydride.

In the prior art, in the gas-phase oxidation for the production of pyromellitic dianhydride, the main catalyst usually is a mixture of vanadium and titanium oxides, namely, vanadium oxide ($V_2O_5$) carried on the surface of titanium oxide ($TiO_2$). It was reported in prior art patent publications that good dispersivity of vanadium oxide is desired in order to obtain high catalytic activity and that the titanium oxide is preferably of anatase. For example, JPA 45-15018 discloses that in the catalyst comprising a mixture of vanadium-molybdenum-phosphorus-titanium oxides, the titanium oxide must be of anatase; and U.S. Pat. No. 4,665,200 further discloses that the anatase should preferably have a surface area of 10~60 m$^2$/g. By using anatase as the support the catalytic activity can be enhanced, however if only vanadium oxide ($V_2O_5$) is employed as the main catalyst, the tetramethylbenzene will be easily over-oxidized into carbon monoxide and carbon dioxide, resulting in a low yield of pyromellitic dianhydride, the temperature difference in the catalyst bed also is uncontrollably high, and hot spots might be formed in the catalyst bed. Various cocatalysts are usually employed to increase the selectivity to pyromellitic dianhydride. For example, U.S. Pat. No. 4,665,200 discloses a catalyst composition based on vanadium-titanium-phosphorus with a mixture of niobium, antimony and an alkali metal being added thereinto; U.S. Pat. No. 4,925,957 and U.S. Pat. No. 5,001,100 disclose catalysts in which mixtures of vanadium-niobium-alkali metal oxides are carried on α-alumina; JPA 5-220398 and JPA 6-63402 disclose a catalyst based on vanadium-beryllium-titanium with a mixture of niobium, bismuth, molybdenum, antimony, tungsten and alkali metal oxides being added thereinto as a cocatalyst; JPA 07-070132 and EP 0,405,508 A2 disclose a vanadium-titanium oxides catalyst carried on an inert substance; and EP 0649677 A1 and EP 0676400 A2 disclose a process for increasing the reaction yield of pyromellitic dianhydride by using a multilayer (i.e., 2~3 layers) catalyst bed, wherein a catalyst of the less active vanadium-phosphorus-potassium oxides mixture is put in the inlet for gaseous 1,2,4,5-tetramethylbenzene, a catalyst of vanadium-phosphorus-titanium oxides mixture is put in the middle part of the bed, and a catalyst of vanadium-molybdenum-phosphorus-titanium oxides mixture is put in the end part of the bed.

The above-mentioned processes though can lead to a high yield of pyromellitic dianhydride, the drawbacks of local overheating and high temperature difference in catalyst beds still can not be effectively overcome and the following problems usually occur: (1) the activity of the catalyst becomes low and thus the reaction should be performed at a high temperature, generally above 400° C., or even up to 500° C., (2) the concentration of the 1,2,4,5-tetraalkylbenzene feedstock should be lower, (3) the catalyst is liable to deactivation because of lost active site by the drastical decrease of surface area of anatase support due to a phase transfer reaction occurred on anatase which is enhanced by the presence of vanadium oxide (see Acad. Sci. Paris, 286c, 135(1978) and Amer. Mineral, 49, 1707(1964)), and (4) further purification steps are necessary to increase the purity of the product since in the product mixture there exist polybasic aromatic acids having low molecular weights, for example benzene tricarboxylic acids, benzene dicarboxylic acids, benzoic acid, etc.

The object of the present invention is to develop a catalyst system which has a stable structure, high catalytic activity and thermal conductivity, and which comprises a mixture of vanadium and tungsten oxides as a main active catalyst; a mixture of rutile and at least one material selected from the group consisting of tungsten carbide, silicon carbide and a mixture thereof as a support; and as a cocatalyst which is a combination of an oxide of a I A and/or II A Group metal, an oxide of manganese, antimony, bismuth, phosphorus, copper, aluminum, titanium or a mixture thereof, and an oxide of a VIII B Group metal. By using this catalyst system in a process for the preparation of pyromellitic dianhydride from 1,2,4,5-tetraalkylbenzene via selective oxidation and the subsequent dehydration in gas phase under normal pressure, pyromellitic dianhydride can be obtained in high yield.

Without any further special purification step, pyromellitic dianhydride in white needle form and having a purity of higher than 98.5% can be obtained by the process of the present invention in which a 1,2,4,5-tetraalkylbenzene is subjected to oxidation and the subsequent dehydration.

The catalyst of the present invention comprises a mixture of vanadium and tungsten oxides dispersed and carried on a support material which is a mixture of rutile and tungsten carbide (or silicon carbide). The selective oxidation is much concerned with the oxidation-reduction property of the catalyst on its surface, and the dehydration is much concerned with the acid-base property of the catalyst on its surface. Another feature of the present invention resides in that by employing the special raw material salts (which may be selected from oxides, nitrates, chlorides, oxalates, acetates and ammonium salts), solvents (which may be selected from aqueous and organic solvents) and calcination temperature and also by adding manganese, chromium, molybdenum, antimony, bismuth, phosphorus, iron, cobalt, nickel, copper, aluminum, titanium or a mixture thereof and an alkali metal and/or alkaline earth metal into the raw material, the oxidation-reduction property and the acid-base property of the catalyst on its surface can be modified. Generally, rutile, tungsten carbide and silicon carbide useful as the support materials have stable structures and high thermal conductivities. However, their surface areas are not high (usually within the range of $1\sim5$ m$^2$/g) so that it is not easy for the mixture of vanadium and tungsten oxides to be uniformly dispersed on the surface of the support. Another technical feature of the present invention is that the surface of the support is first modified by parts of modifying agents or cocatalysts, and then the main catalytic materials are dispersed on the surface of the support to form a uniformly dispersed catalyst having high catalytic activity. There are many methods of preparing the support for the catalysts of this type, among which the representative one is of the co-precipitating method type which comprises the steps of dissolving and mixing salts of aluminum or titanium and I A and II A Group elements in water or an organic solvent, dropping a suspension containing rutile and tungsten carbide or silicon carbide into the resultant mixture, dropping phosphoric acid into the solution to keep the pH in the range of 1.0~6.0, precipitating on the surface of rutile and tungsten carbide (or silicon carbide) the elements having been added, concentrating, drying and molding the raw product into a suitable shape and size, and then calcining the product at 300~1000° C. for several hours to form the desired support for catalyst. The support in the present invention surely can be made by other methods, for example impregnating or kneading methods.

The method of treating the abovesaid support with vanadium-tungsten and other modifying agents is an impregnating method. The support is impregnated with a solution containing vanadium, tungsten and other modifying agents, and then drying and calcining the product at 400~650° C. for several hours to form a catalyst system having high catalytic activity for use in the oxidation of 1,2,4,5-tetraalkylbenzene accompanied by dehydration of the resultant 1,2,4,5-tetracarboxybenzene into pyromellitic dianhydride. Catalysts having properties comparable to the abovesaid one also can be prepared by surface-wetting method or surface-coating method.

The main active components in the catalyst system of the present invention are vanadium and tungsten which constitutes about 1~30% of the total weight of the catalyst system, wherein the atom ratio of vanadium to tungsten is in the range of 1/10~10/1. In this system, the support which carries the main active components on its surface comprises rutile and at least one material selected from the group consisting of tungsten carbide, silicon carbide and a mixture thereof. This support constitutes 99~70%, and preferably of the total weight of the catalyst system, wherein the weight ratio of rutile to tungsten carbide and/or silicon carbide is in the range of 100/0~0/100. Other cocatalysts constitutes 0~15 wt %, preferably 0~10 wt %, of the system, wherein the the atom ratio of chromium to vanadium is in the range of 0/10~1.0/10; atom ratio of manganese to vanadium is in the range of 0/10~4.0/10; the atom ratio of molybdenum to vanadium is in the range of 0/10~5.0/10; the atom ratio of antimony to vanadium is in the range of 0/10~5.0/10; the atom ratio of bismuth to vanadium is in the range of 0/10~5.0/10; the atom ratio of phosphorus to vanadium is in the range of 0.01/10~4.0/10; the atom ratio of iron to vanadium is in the range of 0/10~1.0/10; the atom ratio of cobalt to vanadium is in the range of 0/10~2.0/10; the atom ratio of nickel to vanadium is in the range of 0/10~2.0/10; the atom ratio of copper to vanadium is in the range of 0/10~2.0/10; the atom ratio of aluminum to vanadium is in the range of 0.05/10~5.0/10; the atom ratio of titanium to vanadium is in the range of 0.05/10~5.0/10; the atom ratio of alkali metal (if present in the catalyst system) to vanadium is in the range of 0.01/10~3.0/10; and the atom ratio of alkaline earth metal (if present in the catalyst system) to vanadium is in the range of 0.01/10~3.0/10.

The catalyst prepared by the method of the present invention has a very high activity for selective oxidation. By using this catalyst, 1,2,4,5-tetraalkylbenzene can be selectively oxidized at a lower temperature, and even at a temperature lower than 400° C. the yield of pyromellitic dianhydride still is higher than 80%. In addition, since in the present invention 1,2,4,5-tetraalkylbenzene can be selectively oxidized at a lower temperature, it is less likely that low molecular weight aromatic acids are produced from cracking of the raw material, thereby the final product has a very high purity without the need of further purification treatment.

One of the features of the present invention is that the catalyst has good thermal conductivity, thus even when 1,2,4,5-tetraalkylbenzene feedstock has a high concentration, the temperature difference in the catalyst bed still is lower than 30° C. without the occurrence of local overheating. The oxidation of 1,2,4,5-tetraalkylbenzene is a highly exothermal reaction, for example, the selective oxidation of 1,2,4,5-tetraalkylbenzene into pyromellitic dianhydride has a reaction heat as high as 560 kcal/mol, and its complete oxidation into carbon monoxide or carbon dioxide has a reaction heat as high as 1100 kcal/mol. There come the problems that the temperature difference in the catalyst bed is too high, the operation becomes difficult, local overheating usually occurs and the catalyst is liable to deactivation. In order to solve these problems, in the prior art the oxidation of 1,2,4,5-tetraalkylbenzene is conducted with a lower concentration of 1,2,4,5-tetraalkylbenzene feedstock (<0.2 mol %) and a higher feed gas space-velocity (>10,000 hr$^{-1}$). However, this results in the drawbacks that the yield of pyromellitic dianhydride per unit of catalyst is low and a lot more energy is needed. In the present invention the rutile and tungsten carbide/silicon carbide support has excellent thermal conductivity, therefore at a higher 1,2,4,5-tetraalkylbenzene feedstock concentration (higher than 0.3 mol %), or at a lower feed gas space-velocity (lower than 10,000 hr$^{-1}$), the yield of pyromellitic dianhydride still can reach to higher than 80%.

Another feature of the present invention is that the catalyst has a long life. Owing to the fact that the mixture of rutile and tungsten carbide/silicon carbide acts as support material, the thermal conductivity of the catalyst is improved. Also because rutile has a very stable structure, even if local hot spots are formed in the catalyst bed during the reaction, no crystal phases transfer reaction occurs and the catalyst will not be deactivated. Generally, rutile has a smaller surface area than anatase does, and this makes it more difficult to uniformly disperse catalytic materials, such as vanadium, on the surface of rutile. Therefore, in prior art oxidation of alkylaromatic hydrocarbons, anatase was usually used as catalyst support. However, in the presence of vanadium the crystal structure of anatase becomes very unstable so that the anatase is very liable to conversion into rutile in which the porous structure is destroyed and the surface area is drastically decreased, thereby causing the reduction of the catalytic activity. In the present invention, rutile and tungsten carbide (or silicon carbide) is treated with aluminum or titanium and an alkali metal to form on the surface a coating onto which catalytically active substances, such as vanadium, can be well dispersed. Thereafter, the surface of the coating is impregnated with substances containing catalytically active substances, such as vanadium and tungsten, and thus a catalyst having very high catalytic activity useful in the oxidation of alkylaromatic hydrocarbon is obtained. The catalyst firmly adheres to the support and the problem of detachment does not occur.

In the present invention, the reaction is carried out continuously in a fixed-bed reactor which is connected to a product collector which is in hollow-tube shape and is equipped with a temperature controlling means to maintain a two-stage temperature profile. 1,2,4,5-tetraalkylbenzene which has been heated and melted into a melt is directly pumped into a preheater in which it is mixed with air to form the feedstock having a concentration of 0.1~1.0 mol %. The flow rate of the gaseous feedstock (expressed as space-velocity for the gas phase) is 4,000~14,000 hr$^{-1}$, preferably 6,000~10,000 hr$^{-1}$, and the reaction temperature is 300~450° C., preferably 320~390° C. In the reaction, the oxidant is molecular oxygen in air, and other inert gases, such as nitrogen, carbon monoxide or carbon dioxide, are used for diluting the molecular oxygen in air. The reaction pressure is lower than 5 atm, preferably lower than 1 atm.

To aid in understanding the advantages and feasibility of the present invention, the following Examples and Comparative Examples are provided in which the excellent properties of the catalyst system in the present invention are demonstrated and also are compared with that of the prior art catalysts. The reactions are carried out in a fixed-bed reactor under normal pressure. The reactor is a stainless steel tube having an outside diameter of 1 inch and a length of 60 cm, and a catalyst bed height of 10~15 cm. The temperature of the preheating zone outside the reactor tube is controlled at 300° C. by a heating zone, and the temperature of the reactor is controlled at 300~450° C. by an electric furnace. The raw material, 2,4,5-tetraalkylbenzene, is pumped into the upper portion of the reactor to be mixed with air or an inert gas in the desired ratio and then is subjected to reaction with the space-velocity being controlled by a mass flow meter. The gaseous product after having been cooled to 250° C. is allowed to enter the first product collector in the shape of a hollow tube in which the temperature is maintained at 170~190° C. After the majority of pyromellitic dianhydride thus produced has been collected, the gaseous product is discharged from the top and is allowed to enter the second product collector in the shape of a hollow tube in which the temperature is maintained at 100~130° C. After the product is collected, the gaseous end product is condensed in a condenser and collected with a gas collecting bag. The solid product is dissolved in tetrahydrofuran and is subjected to liquid chromatography. The carbon monoxide and carbon dioxide in the gaseous product is quantitatively determined in a gas chromatographer by using the external standard method.

In the following Examples and Comparative Examples, the conversion ratio and the yield of pyromellitic dianhydride are calculated in accordance with formulae (1) and (2), respectively:

$$\text{conversion ratio of pyromellitic dianhydride (\%)} = \frac{(\text{amount of the 1,2,4,5-tetraalkylbenzene feedstock}) - (\text{the residual amount of 1,2,4,5-tetraalkylbenzene in the product})}{(\text{amount of the 1,2,4,5-tetraalkylbenzene feedstock})} \times 100\% \quad (1)$$

$$\text{yield of pyromellitic dianhydride (\%)} = \frac{(\text{amount of pyromellitic dianhydride in the product})}{(\text{amount of the 1,2,4,5-tetraalkylbenzene feedstock})} \times 100\% \quad (2)$$

The following Examples are intended to elucidate the preferred embodiments, but not to represent the complete scope, of the present invention. Any obvious modifications made by those skilled in the art on the basis of the technical content disclosed in this specification should be considered within the scope of patent protection of the present invention.

EXAMPLE 1

60 g of rutile and 30 g of tungsten carbide were ground together by a mill, and 300 ml of water was added into the mixture to form a slurry. An aqueous solution consisting of 50 ml of water, 18.3 g of aluminum nitrate, 2 g of calcium chloride and 0.05 g of potassium hydroxide was slowly dropped into the slurry, and the pH was adjusted to 5.0~6.0 by using a 80% aqueous solution of phosphoric acid. The resultant mixture was heated and refluxed for 1 hour, then dried and molded into granules having a diameter of 2 mm and a length of 3~5 mm, and finally calcined at 400° C. for 3 hours into a desired catalyst support. 10 g of V$_2$O$_5$ was dissolved in a mixture of 300 ml of water and 30 g of oxalic acid with the aid of heating, and 24.6 g of ammonium tungstate was added into the solution. The abovesaid catalyst support was immersed in this solution for 5 hours, then the liquid was evaporated off, and the remaining material was calcined in an air stream at 500° C. for 5 hours.

30 ml of the catalyst produced as stated above was filled into a reactor, then the preheating zone was maintained at the temperature of 300° C., and the reaction temperature at 330° C. 1,2,4,5-tetramethylbenzene with an concentration of 30 g/NM³ was mixed with air and subjected to reaction with a space-velocity of 6000 hr⁻¹ for 6 hours to obtain a white needle product containing pyromellitic dianhydride. Results of analysis showed that the yield of pyromellitic dianhydride was 85%; the selectivities to CO and $CO_2$ were 5.3 mol % and 19.6 mol %, respectively; and the purity of the product was 99.3%. The maximum temperature difference in the catalyst bed was 30° C.

EXAMPLE 2

30 g of rutile and 60 g of silicon carbide were ground together by a mill, and 300 ml of water was added into the mixture to form a slurry. An aquogel containing 17.3 g of $TiCl_4$ and 10 g of silicon was added into the slurry with stirring. 5 g of calcium chloride and 0.05 g of potassium hydroxide were added in sequence, and the pH was adjusted to 1.0~1.5 by using a 80% aqueous solution of phosphoric acid. The resultant mixture was heated and refluxed for 1 hour, then dried and molded into granules having a diameter of 2 mm and a length of 3~5 mm, and finally calcined at 400° C. for 3 hours into the desired catalyst support. 11.7 g of ammonium vanadate was dissolved in a mixture of 300 ml of water and 30 g of oxalic acid with the aid of heating, and 49.2 g of ammonium tungstate was added into the solution. The abovesaid catalyst support was immersed in this solution for 3 hours, then the liquid was evaporated off, and the remaining material was calcined in an air stream at 530° C. for 8 hours.

30 ml of the catalyst produced as stated above was filled into a reactor, then the preheating zone was maintained at the temperature of 300° C., and the reaction temperature at 350° C. 1,2,4,5-tetramethylbenzene with a concentration of 60 g/NM³ was mixed with air and subjected to reaction with a space-velocity of 8000 hr⁻¹ to obtain a white needle product containing pyromellitic dianhydride. Results of analysis showed that the yield of pyromellitic dianhydride was 90%, and the purity of the product was 99.1%. The temperature difference in the catalyst bed during the reaction was 26° C.

COMPARATIVE EXAMPLE 1

10 g of $V_2O_5$ was dissolved in a mixture of 300 ml of water and 30 g of oxalic acid with the aid of heating. 24.6 g of ammonium tungstate and an aqueous 80% phosphoric acid were added to form a solution, and then 90 g of rutile was added. The liquid was evaporated off, and the remaining material was calcined in an air steam at 500° C. for 5 hours.

A reaction was conducted in the same manner as in Example 1. Pyromellitic dianhydride was thus obtained in a yield of 15% and a purity of 98.3%. The temperature difference in the catalyst bed during the reaction was 50° C.

COMPARATIVE EXAMPLE 2

A reaction was conducted in the same manner as in Comparative Example 1 by using the same catalyst except that the reaction temperature was 420° C., the concentration of 1,2,4,5-tetramethylbenzene feedstream was 10 g/NM³ and the gas space-velocity was 12,000 hr⁻¹. As a result, pyromellitic dianhydride product (which had a yellowish-brown color) was obtained in a yield of 78% and a purity of 98.3%. The temperature difference in the catalyst bed during the reaction was 90° C.

COMPARATIVE EXAMPLE 3

11.7 g of ammonium vanadate was dissolved in a mixture of 300 ml of water and 30 g of oxalic acid. 0.75 g of ammonium phosphate and 0.56 g of niobium pentachloride were added, and then 5.5 g of $SnO_2$ and 90 g of anatase were added to form a slurry. This slurry was sprayed on the surfaces of 100 ml of silicon carbide platelets having an average diameter of 2~3 mm to form a catalyst coating thereon. The coated silicon carbide platelets were calcined in an air steam at 530° C. for 8 hours.

A reaction was conducted in the same manner as in Example 2 by using the catalyst produced above. As a results, pyromellitic dianhydride product was thus obtained in a yield of 52% and a purity of 99.4%. The temperature difference in the catalyst bed during the reaction was 150° C.

EXAMPLE 3

A catalyst support was prepared by using 20 g of rutile and 70 g of silicon carbide in the manner as in Example 2. Next, 5.8 g of ammonium vanadate was dissolved in a mixture of 300 ml of water and 30 g of oxalic acid, then 73.8 g of ammonium tungstate, 3 g of cupric nitrate (Cu(II) nitrate), 1.8 g of manganous nitrate (Mn(II) nitrate) and 1.5 g of nickelous sulfate (Ni(II) sulfate) were added in sequence in the same manner as in Example 2 to obtain a catalyst. A reaction was conducted in the same manner as in Example 2. As a result, the pyromellitic dianhydride product was thus obtained in a yield of 95% and a purity of 99.3%. The temperature difference in the catalyst bed during the reaction was 24° C.

EXAMPLE 4

A catalyst was prepared and a reaction was conducted in the same manner as in Example 3, except that the catalyst was calcined at 600° C. for 10 hours. The results are shown in Table 1.

EXAMPLE 5

A catalyst was prepared and a reaction was conducted in the same manner as in Example 1, except that in the preparation of the catalyst 4.9 g of bismuth nitrate (Bi(III) nitrate) and 6.0 g of antimonic chloride ($SbCl_5$) were added into the solution containing $V_2O_5$ and ammonium tungstate, and that the reaction was conducted with a gas space-velocity of 4,000 hr⁻¹ at 310° C. The results are shown in Table 1.

EXAMPLE 6

A catalyst was prepared in the same manner as in Example 2, except that in the preparation of the catalyst support 85 g of rutile and 5 g of silicon carbide were used. 23.4 g of ammonium vanadate, 12.3 g of ammonium tungstate and 2 g of ferric sulfate (Fe(III) sulfate) were dissolved in 300 ml of water, and the abovesaid catalyst support was immersed in this solution to prepare catalyst granules. A reaction was conducted in the same manner as in Example 5, except that the reaction temperature was 390° C. The results are shown in Table 1.

EXAMPLE 7

30 g of rutile, 50 g of silicon carbide and 10 g of tungsten carbide were ground together, and 300 ml of water was added into the mixture to form a slurry. 8.7 g of $TiCl_4$ and 4.6 g aluminum nitrate were added, and the pH was adjusted to 1.5 by nitric acid. The resultant mixture was heated and refluxed for 1 hour, then dried and molded into granules having a diameter of 2~3 mm, and finally calcined at 400° C. for 3 hours into a desired catalyst support. 11.7 g of ammonium vanadate was dissolved in a mixture of 300 ml of water and 30 g of oxalic acid, then 12.3 g of ammonium tungstate, 0.75 g of ammonium phosphate and 6 g of cobaltous nitrate (Co(II) nitrate) were added into the solution. The abovesaid catalyst support was immersed in this solution, and a catalyst was prepared in the same manner as in Example 1. Also, a reaction was conducted in the same manner as in Example 1, except that the 1,2,4,5-tetramethylbenzene feedstream is in a concentration of 80 g/NM$^3$, the reaction temperature was 370° C. and the gas feedstream was in a space-velocity of 10,000 hr$^{-1}$. The results are shown in Table 1.

EXAMPLE 8

A catalyst was prepared and a reaction was conducted in the same manner as in Example 7, except that the catalyst was calcined at 700° C. for 3 hours. The results are shown in Table 1.

EXAMPLE 9

A catalyst was prepared and a reaction was conducted in the same manner as in Example 7, except that 7 g of ammonium vanadate, 0.4 g of ammonium phosphate and 8.5 g of manganic nitrate (Mn(II) nitrate) were used as the components of the catalyst. The thus obtained catalyst was subjected to the reaction where the concentration of the 1,2,4,5-tetramethylbenzene feedstream was 30 g/NM$^3$ and the gas space-velocity was 6,000 hr$^{-1}$. The results are shown in Table 1.

EXAMPLE 10

A catalyst was prepared and a reaction was conducted in the same manner as in Example 2, except that 11.7 g of ammonium vanadate, 3.1 g of ammonium tungstate, 0.85 g ammonium phosphate, 3 g of cupric nitrate (Cu(II) nitrate) and 2.5 g of ammonium dichromate were used as the components of the catalyst. The results are shown in Table 1.

COMPARATIVE EXAMPLE 4

A catalyst was prepared in the same manner as in Example 2 except that rutile was replaced by anatase. A reaction was conducted in the same manner as in Example 7. The results are shown in Table 1.

COMPARATIVE EXAMPLE 5

A catalyst was prepared and a reaction was conducted in the same manner as in Comparative Example 4, except that the catalyst was calcined at 700° C. for 3 hours. The results are shown in Table 1.

EXAMPLE 11

A catalyst was prepared and a reaction was conducted in the same manner as in Example 1, except that the ratio of air (which acted as an oxidant) to nitrogen was 1:1. As a result, pyromellitic dianhydride product was obtained in a yield of 94% and a purity of 98.0%.

EXAMPLE 12

A catalyst was prepared and a reaction was conducted in the same manner as in Example 1, except that air (which acted as an oxidant) was replaced by a mixture of air and $CO_2$ in an ratio of 2:1. As a result, pyromellitic dianhydride product was obtained in a yield of 87% and a purity of 99.3%.

EXAMPLE 13

A catalyst was prepared and a reaction was conducted in the same manner as in Example 1, except that 1,2,4,5-tetramethylbenzene was replaced by 1-propyl-2,4,5-trimethylbenzene, and that air (which acted as an oxidant) was replaced by a mixture of air and nitrogen in an ratio of 3:1. As a result, pyromellitic dianhydride product was obtained in a yield of 92% and a purity of 99.5%.

EXAMPLE 14

A catalyst was prepared and a reaction was conducted in the same manner as in Example 1, except that 1,2,4,5-tetramethylbenzene was replaced by 1-ethyl-2,4,5-trimethylbenzene, and that air (which acted as an oxidant) was replaced by a mixture of air and $NO_2$ in an ratio of 1:1. As a result, the pyromellitic dianhydride product was obtained in a yield of 86% and a purity of 98.6%.

EXAMPLE 15

A catalyst was prepared and a reaction was conducted in the same manner as in Example 2, except that 1,2,4,5-tetramethylbenzene was replaced by 1-methyl-2,4,5-triethylbenzene. As a result, pyromellitic dianhydride product was obtained in a yield of 90% and a purity of 98.8%.

TABLE 1

| | heating temperature in the reactor tube (° C.) | highest temperature in the catalyst bed (° C.) | temperature difference in the catalyst bed (° C.) | concentration of 1,2,4,5-tetramethylbenzene (g/NM$^3$) | gas space-velocity (hr$^{-1}$) | crystal state of the catalyst[1] | specific surface area[2] | yield of pyromellitic dianhydride (%) |
|---|---|---|---|---|---|---|---|---|
| Example 4 | 350 | 375 | +25 | 60 | 8,000 | rutile | 3.8 | 92.9 |
| Example 5 | 310 | 325 | +15 | 30 | 4,000 | rutile | 4.6 | 98 |
| Example 6 | 370 | 400 | +30 | 30 | 8,000 | rutile | 4.9 | 100 |
| Example 7 | 370 | 390 | +20 | 80 | 10,000 | rutile | 2.4 | 83.4 |
| Example 8 | 370 | 388 | +18 | 80 | 10,000 | rutile | 4.2 | 89 |
| Example 9 | 350 | 385 | +15 | 30 | 6,000 | rutile | 4.0 | 96 |
| Example 10 | 350 | 380 | +30 | 60 | 8,000 | rutile | 3.9 | 93 |
| Comparative Example 4 | 370 | 510 | +140 | 80 | 10,000 | anatase | 10.8 | 49.6 |
| Comparative Example 5 | 370 | 400 | +30 | 80 | 10,000 | rutile | 0.9 | 15.1 | note
[1] crystal state of the catalyst was analyzed with XRD method
[2] specific surface area was analyzed with BET nitrogen adsorption method Table 1 shows that by using the catalyst system of the present invention in the oxidation of 1,2,4,5-tetraalkylbenzene, the yield of pyromellitic dianhydride was high, the temperature difference in the catalyst bed was low, and upon high temperature treatment the crystal structure of the titanium oxide ($TiO_2$) in the catalyst system did not change and thus the catalyst was not liable to deactivation. In comparison, when using a catalyst system comprising anatase as the catalyst support, temperature difference in the catalyst bed was high, and under a high temperature the crystal structure of anatase became unstable and tended to turn into rutile. Also, both the specific surface area and catalytic activity of the catalyst drastically decreased.

What is claimed is:

1. A process for the preparation of pyromellitic dianhydride, comprising:
   (a) providing a feedstream containing a 1,2,4,5-tetraalkylbenzene of the formula

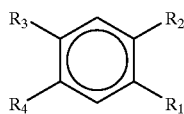

where $R_1$ is $CH_3$, and $R_2$, $R_3$ and $R_4$ are each independently $C_1$–$C_3$ alkyl groups, and
   (b) subjecting the 1,2,4,5-tetraalkylbenzene in the feedstream to a selective oxidation at 300~450° C. in the presence of a catalyst system comprising a catalyst support comprising rutile and at least one material selected from the group consisting of tungsten carbide, silicon carbide and a mixture thereof; a catalyst which is a mixture of vanadium and tungsten oxides; and a cocatalyst which is a combination of an oxide of an element of the I A and/or II A group of the periodic table, an oxide of manganese, antimony, bismuth, phosphorus, copper, aluminum, titanium or a mixture thereof, and an oxide of an element of the VIII B Group of the periodic table;

wherein said catalyst and cocatalyst in combination has the formula:

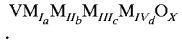

wherein:
   V is vanadium;
   $M_I$ is tungsten;
   $M_{II}$ is manganese, antimony, bismuth, phosphorus, copper, aluminum, titanium or a mixture thereof;
   $M_{III}$ is an element of the VIIIB group of the periodic table;
   $M_{IV}$ is an alkali metal and/or an alkaline earth metal; and
   X is a value within the range of from 7 to 40.

2. The process of claim 1, wherein the 1,2,4,5-tetraalkylbenzene is in a concentration of 0.1~1 mol % and is 1,2,4,5-tetramethylbenzene, 1-ethyl-2,4,5-trimethylbenzene or 1-propyl-2,4,5-trimethylbenzene.

3. The process of claim 1, wherein the catalyst support constitutes 99~70% of the total weight of the catalyst system and comprises rutile and at least on material selected from the group consisting of tungsten carbide, silicon carbide and a mixture thereof.

4. The process of claim 3, wherein the surface of the catalyst support is treated with an aluminum compound, a titanium compound, an acid or a base.

5. The process of claim 1, wherein in the catalyst system vanadium is in an amount of 1~30 wt %, $M_I$ is tungsten, and the atom ratio of vanadium to tungsten is in the range of 1/10~10/1.

6. The process of claim 1, wherein in the catalyst system $M_{II}$ is in an amount of 0~15 wt % and is selected from the group consisting of manganese, phosphorus, antimony, bismuth, copper, aluminum, titanium and mixtures thereof; and wherein in the catalyst system the atom ratio of manganese to vanadium is in the range of 0/10~4.0/10, the atom ratio of antimony to vanadium is in the range of 0/10~5.0/10, the atom ratio of bismuth to vanadium is in the range of 0/10~5.0/10, the atom ratio of phosphorus to vanadium is in the range of 0.01/10~4.0/10, the atom ratio of copper to vanadium is in the range of 0/10~2.0/10, the atom ratio of aluminum to vanadium is in the range of 0.05/10~5.0/10, and the atom ratio of titanium to vanadium is in the range of 0.05/10~5.0/10.

7. The process of claim 1, wherein in the catalyst system $M_{IV}$ is in an amount of 0~5 wt % and is selected from the group consisting of potassium, cerium, rubidium, magnesium and calcium.

8. The process of claim 1, which is carried out in a fixed bed.

9. The process of claim 1, wherein in the selective oxidation a gaseous oxidant is used which is selected from the group consisting of air, molecular oxygen and a mixture of air and at least one inert gas.

10. The process of claim 1, wherein the feedstream is in a gas flow space velocity of 4,000~14,000 $hr^{-1}$.

* * * * *

UNITED STATES PATENT AND TRADEMARK OFFICE
CERTIFICATE OF CORRECTION

PATENT NO. : 6,084,109
DATED : July 4, 2000
INVENTOR(S) : Shiao-Jung Chu and Chian-Liang Hwang It is certified that error appears in the above-identified patent and that said Letters Patent is hereby corrected as shown below:

Column 6,
Line 28, replace "2-5" with -- - --.

Claim 1,
Line 31, (Column 12, line 3), After "40", please insert the following:
"a" is a value within the range of from 0.1 to 10;
"b" is a value within the range of from 0.01 to 1;
"c" is a value within the range of from 0 to 0.5;
"d" is a value within the range of from 0.01 to 0.6.

Signed and Sealed this

Ninth Day of October, 2001

Attest:

NICHOLAS P. GODICI
Attesting Officer
Acting Director of the United States Patent and Trademark Office